US012674106B2

(12) United States Patent
Harandi et al.

(10) Patent No.: US 12,674,106 B2
(45) Date of Patent: Jul. 7, 2026

(54) PROCESSES AND SYSTEMS FOR CONVERTING A HYDROCARBON-CONTAINING FEED

(71) Applicant: ExxonMobil Chemical Patents Inc., Baytown, TX (US)

(72) Inventors: Mohsen N. Harandi, Calgary (CA); Michael F. Raterman, Doylestown, PA (US); Paul F. Keusenkothen, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 985 days.

(21) Appl. No.: 17/778,202

(22) PCT Filed: Nov. 11, 2020

(86) PCT No.: PCT/US2020/059931
§ 371 (c)(1),
(2) Date: May 19, 2022

(87) PCT Pub. No.: WO2021/118741
PCT Pub. Date: Jun. 17, 2021

(65) Prior Publication Data
US 2023/0016743 A1    Jan. 19, 2023

Related U.S. Application Data

(60) Provisional application No. 62/946,746, filed on Dec. 11, 2019.

(51) Int. Cl.
*C10K 1/00* (2006.01)
*C01B 3/025* (2026.01)
(Continued)

(52) U.S. Cl.
CPC .............. *C10K 1/005* (2013.01); *C01B 3/025* (2013.01); *C01C 1/0488* (2013.01);
(Continued)

(58) Field of Classification Search
CPC .......... C10K 1/005; C10K 1/004; C10K 3/04; C01B 3/025; C01B 2203/0205;
(Continued)

(56) References Cited

U.S. PATENT DOCUMENTS 4,675,098 A    6/1987 Miyauchi et al. ............ 208/127
4,828,681 A    5/1989 Yourtee et al. ............... 208/127
(Continued)

FOREIGN PATENT DOCUMENTS

CN        108587674    9/2018 ............... C10G 9/28
WO    WO2018/111574    6/2018 ............. C10G 45/00
(Continued)

*Primary Examiner* — Anthony J Zimmer
*Assistant Examiner* — Starfari Teshawn Mcclain
(74) *Attorney, Agent, or Firm* — WOMBLE BOND DICKINSON (US) LLP; Kevin Davis

(57) ABSTRACT

Processes and systems for converting a hydrocarbon-containing feed. The feed and heated particles can be contacted within a pyrolysis zone to effect pyrolysis of at least a portion of the feed to produce a pyrolysis zone effluent and a first gaseous stream rich in olefins and a first particle stream rich in the particles can be obtained therefrom. At least a portion of the first particle stream, an oxidant, and steam can be fed into a gasification zone and contacted therein to effect gasification of at least a portion of coke disposed on the surface of the particles to produce a gasification zone effluent. A second gaseous stream rich in a synthesis gas and a second particle stream rich in heated and regenerated particles can be obtained from the gasification zone effluent. At least a portion of the second particle stream can be fed into the pyrolysis zone.

23 Claims, 1 Drawing Sheet

(51) Int. Cl.

| | |
|---|---|
| *C01C 1/04* | (2006.01) |
| *C07C 29/151* | (2006.01) |
| *C07C 273/04* | (2006.01) |
| *C07C 273/10* | (2006.01) |
| *C10B 49/22* | (2006.01) |
| *C10B 55/10* | (2006.01) |
| *C10G 9/32* | (2006.01) |
| *C10J 3/46* | (2006.01) |
| *C10J 3/62* | (2006.01) |

(52) U.S. Cl.
CPC ........ *C07C 29/1518* (2013.01); *C07C 273/04* (2013.01); *C07C 273/10* (2013.01); *C10B 49/22* (2013.01); *C10B 55/10* (2013.01); *C10G 9/32* (2013.01); *C10J 3/46* (2013.01); *C10J 3/62* (2013.01); *C01B 2203/0205* (2013.01); *C01B 2203/0283* (2013.01); *C01B 2203/0475* (2013.01); *C01B 2203/061* (2013.01); *C10G 2400/20* (2013.01); *C10G 2400/22* (2013.01); *C10J 2300/0943* (2013.01); *C10J 2300/0956* (2013.01); *C10J 2300/0959* (2013.01); *C10J 2300/0976* (2013.01); *C10J 2300/0989* (2013.01); *C10J 2300/0993* (2013.01); *C10J 2300/1612* (2013.01); *C10J 2300/1665* (2013.01); *C10J 2300/1668* (2013.01); *C10J 2300/1678* (2013.01); *C10J 2300/1693* (2013.01); *C10J 2300/1807* (2013.01); *C10J 2300/1823* (2013.01); *C10J 2300/1838* (2013.01)

(58) Field of Classification Search
CPC .... C01B 2203/0283; C01B 2203/0475; C01B 2203/061; C01C 1/0488; C01C 1/0405; C07C 29/1518; C07C 273/04; C07C 273/10; C10B 49/22; C10B 55/10; C10B 49/20; C10B 53/07; C10B 55/04; C10B 57/06; C10G 9/32; C10G 2400/20; C10G 2400/22; C10J 3/46; C10J 3/62; C10J 2300/0943; C10J 2300/0956; C10J 2300/0959; C10J 2300/0976; C10J 2300/0989; C10J 2300/0993; C10J 2300/1612; C10J 2300/1665; C10J 2300/1668; C10J 2300/1678; C10J 2300/1693; C10J 2300/1807; C10J 2300/1823; C10J 2300/1838; Y02P 20/52
See application file for complete search history.

(56) References Cited

U.S. PATENT DOCUMENTS

| | | | | |
|---|---|---|---|---|
| 4,939,314 | A * | 7/1990 | Harandi | ................... C07C 2/00 |
| | | | | 585/533 |
| 6,419,885 | B1 | 7/2002 | Di Nicolantonio et al. | . 422/198 |
| 7,090,081 | B2 | 8/2006 | Vaughn et al. | ............... 209/154 |
| 7,309,383 | B2 | 12/2007 | Beech et al. | .................... 95/268 |
| 7,674,366 | B2 | 3/2010 | Strack et al. | ................... 208/48 |
| 7,718,049 | B2 | 5/2010 | Strack et al. | ................... 208/48 |
| 7,993,435 | B2 | 8/2011 | Stell et al. | ...................... 96/293 |
| 8,105,479 | B2 | 1/2012 | Ou et al. | ......................... 208/44 |
| 9,358,516 | B2 | 6/2016 | Tammera et al. | .......... B01J 8/20 |
| 9,637,694 | B2 | 5/2017 | Evans et al. | ........... C10G 69/06 |
| 9,777,227 | B2 | 10/2017 | Soultanidis et al. | ... C10G 49/00 |
| 10,407,631 | B2 | 9/2019 | Harandi et al. | .......... C10J 3/466 |
| 11,352,567 | B2 | 6/2022 | Harandi et al. | .......... C10G 1/10 |
| 2015/0141699 | A1 * | 5/2015 | Barger | ...................... C10C 1/16 |
| | | | | 568/429 |
| 2018/0170832 | A1 | 6/2018 | Janda et al. | ............. C07C 4/04 |
| 2019/0144768 | A1 * | 5/2019 | Harandi | .............. C07C 29/1518 |
| | | | | 518/703 |
| 2022/0275283 | A1 | 9/2022 | Raterman et al. | ....... C10G 9/32 |

FOREIGN PATENT DOCUMENTS

| | | | | |
|---|---|---|---|---|
| WO | WO2019/099247 | | 5/2019 | ............... C10J 3/84 |
| WO | WO2019/106784 | | 7/2020 | ............ C01B 3/382 |

* cited by examiner

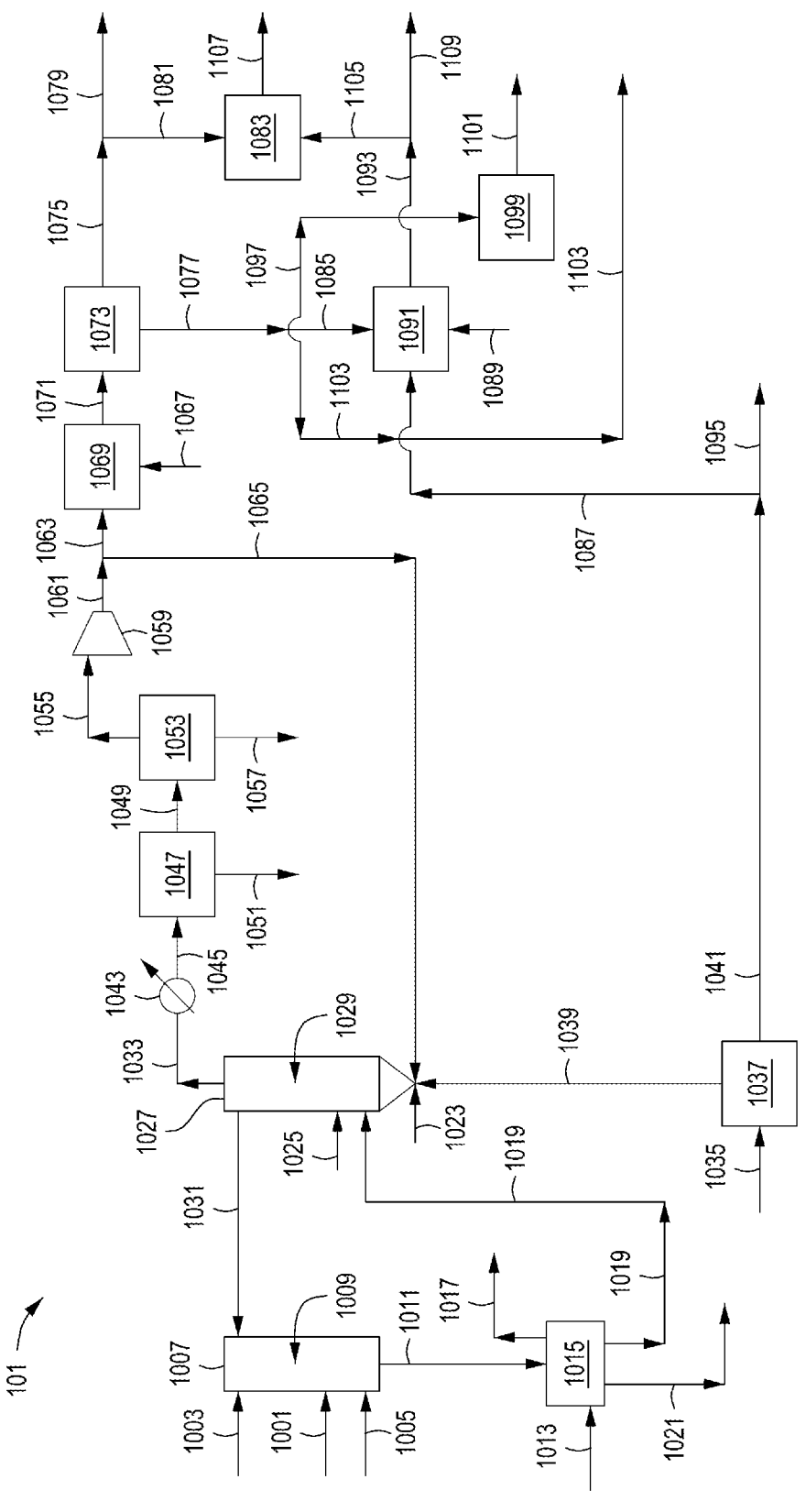

PROCESSES AND SYSTEMS FOR CONVERTING A HYDROCARBON-CONTAINING FEED

CROSS-REFERENCE TO RELATED APPLICATIONS

This application is a US national phase application of PCT Application Serial No. PCT/US2020/059931 having a filing date of Nov. 11, 2020, which claims priority to and the benefit of U.S. Provisional Application No. 62/946,746 having a filing date of Dec. 11, 2019, the disclosures of all of which are incorporated herein by reference in their entireties.

FIELD

This disclosure relates to processes and systems for converting a hydrocarbon-containing feed. In particular, this disclosure relates to processes and systems for converting a hydrocarbon-containing feed by pyrolysis and gasification to produce various products, e.g., olefins and synthesis gas.

BACKGROUND

Steam cracking, also referred to as pyrolysis, has long been used to crack various hydrocarbon-containing feeds into olefins, preferably light olefins such as ethylene, propylene, and butenes. Conventional steam cracking utilizes a pyrolysis furnace ("steam cracker") that has two main sections: a convection section and a radiant section. The hydrocarbon-containing feed typically enters the convection section of the furnace as a liquid (except for light feedstocks that typically enter as a vapor) where the hydrocarbon-containing feed is typically heated and vaporized by indirect heat exchange with a hot flue gas from the radiant section and by direct contact with steam. The vaporized hydrocarbon-containing feed and steam mixture is fed into the radiant section where the cracking takes place. The resulting pyrolysis zone effluent, including olefins, leaves the pyrolysis furnace for further downstream processing, including quenching.

Conventional steam crackers do not have the flexibility to process residues, crudes, or many crude gas oils or naphthas that are contaminated with non-volatile components. Non-volatile components, if present in the feed, typically cause fouling within the radiant section of the pyrolysis furnace. An external vaporization or flash drum has been implemented to separate vaporized hydrocarbons from liquid hydrocarbons to address the fouling problems in the steam cracker. The vaporized hydrocarbons are then cracked in the steam cracker and the liquid hydrocarbons that include nonvolatile components are removed and used as fuel. The liquid hydrocarbons, however, still contain a substantial quantity of hydrocarbons which, if converted into higher-value lighter hydrocarbons such as olefins via cracking, would bring substantial additional value to the crude oil feed. Thus, for decades the petrochemical industry has been trying to take advantage of relatively low-cost heavy crude oil to make substantial quantities of valuable chemicals such as olefins. The large amount of non-volatiles in the low-cost heavy crude oil, however, requires extensive and expensive processing.

There is a need, therefore, for improved processes and systems for converting hydrocarbon-containing feeds, e.g., petroleum feeds that include a resid, to produce valuable chemical products. This disclosure satisfies this and other needs.

SUMMARY

The present inventors have devised processes and systems for converting a hydrocarbon-containing feed. In some examples, the process can include feeding the hydrocarbon-containing feed and heated particles into a pyrolysis zone. The hydrocarbon-containing feed can be contacted with the heated particles in the pyrolysis zone to effect pyrolysis of at least a portion of the hydrocarbon-containing feed to produce a pyrolysis zone effluent. The pyrolysis zone effluent can include olefins and the particles. Coke can be formed on the surface of the particles. In some examples, a velocity of gaseous components within the pyrolysis zone can be at least 20% greater than a velocity of the particles within the pyrolysis zone. A first gaseous stream rich in the olefins and a first particle stream rich in the particles can be obtained from the pyrolysis zone effluent. At least a portion of the first particle stream, an oxidant stream, and a steam stream can be fed into a gasification zone. The first particle stream, the oxidant stream, and the steam stream can be contacted within the gasification zone to effect gasification of at least a portion of the coke disposed on the surface of the particles to produce a gasification zone effluent. The gasification zone effluent can include the heated and regenerated particles and a synthesis gas. The synthesis gas can include molecular hydrogen, carbon monoxide, and carbon dioxide. A second gaseous stream rich in the synthesis gas and a second particle stream rich in the heated and regenerated particles can be obtained from the gasification zone effluent. At least a portion of the second particle stream can be fed into the pyrolysis zone as at least a portion of the heated particles fed into the pyrolysis zone.

In some examples, the system for converting a hydrocarbon-containing feed can include a pyrolysis reactor having a pyrolysis zone adapted for receiving the hydrocarbon-containing feed and a heated particles, allowing the hydrocarbon-containing feed to contact the particles to effect pyrolysis of at least a portion of the hydrocarbon-containing feed and to form coke on the surface of the particles to produce a pyrolysis zone effluent comprising olefins and the particles while maintaining a velocity of gaseous components within the pyrolysis zone that is at least 20% greater than a velocity of the particles within the pyrolysis zone. The system can also include a first separation device adapted for receiving the pyrolysis zone effluent, optionally receiving a stripping steam stream, separating the pyrolysis zone effluent to obtain a first gaseous stream rich in the olefins and a first particle stream rich in the particles, discharging the first gaseous stream, and discharging the first particle stream. The system can also include a first channel adapted for feeding at least a portion of the first particle stream to a gasification zone. The system can also include a gasifier that can include the gasification zone, the gasification zone adapted for receiving the first particle stream, an oxidant stream, and a steam stream, and gasifying at least a portion of the coke disposed on the surface of the particles to produce a gasification zone effluent comprising heated and regenerated particles and a synthesis gas, wherein the synthesis gas comprises molecular hydrogen, carbon monoxide, and carbon dioxide, discharging a second gaseous stream rich in the synthesis gas, and discharging a second particle stream rich in the heated and regenerated particles. The system can also include a second channel adapted for feeding at least a portion of the heated and regenerated particles to the pyrolysis reactor such that the regenerated and heated particles make up at least a portion of the heated particles contacted with the hydrocarbon-containing feed in the pyrolysis zone.

BRIEF DESCRIPTION OF THE DRAWINGS

The FIGURE depicts an illustrative system for processing a hydrocarbon-containing feed, according to one or more embodiments described.

DETAILED DESCRIPTION

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other steps, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and/or equipment used for acquiring the measurement.

Certain embodiments and features are described herein using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated.

As used herein, the indefinite article "a" or "an" shall mean "at least one" unless specified to the contrary or the context clearly indicates otherwise. Thus, embodiments using "a pyrolysis reactor" include embodiments where one, two or more pyrolysis reactors are used, unless specified to the contrary or the context clearly indicates that only one pyrolysis reactor is used.

The term "hydrocarbon" as used herein means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). Thus, a C2 hydrocarbon can be ethane, ethylene, acetylene, or mixtures of at least two of these compounds at any proportion. A "Cm to Cn hydrocarbon" or "Cm-Cn hydrocarbon," where m and n are positive integers and m<n, means any of Cm, Cm+1, Cm+2, . . . , Cn−1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon" can be ethane, propane, cyclopropane, or any mixture thereof of two or more thereof at any proportion. A "Cn+ hydrocarbon" means (i) any hydrocarbon compound comprising carbon atom(s) in its molecule at the total number of at least n, or (ii) any mixture of two or more such hydrocarbon compounds in (i). A "Cn− hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s).

The term "non-volatile components" as used herein refers to the fraction of a petroleum feed having a nominal boiling point of at least 590° C., as measured by ASTM D6352-15 or D-2887-18. Non-volatiles include coke precursors, which are large, condensable molecules that condense in the vapor and then form coke during pyrolysis of the petroleum feed.

The term "crude" as used herein means whole crude oil as it flows from a wellhead, a production field facility, a transportation facility, or other initial field processing facility, optionally including crude that has been processed by a step of desalting, treating, and/or other steps as may be necessary to render it acceptable for conventional distillation in a refinery. Crude, as used herein, is presumed to contain resid. The term "crude fraction", as used herein, means a hydrocarbon fraction obtained via the fractionation of crude.

The term "resid" as used herein refers to a bottoms cut of a crude distillation process that contains non-volatile components. Resids are complex mixtures of heavy petroleum compounds otherwise known in the art as residuum or residual. Atmospheric resid is the bottoms product produced from atmospheric distillation of crude where a typical end-point of the heaviest distilled product is nominally 343° C., and is referred to as 343° C. resid. The term "nominally", as used herein, means that reasonable experts may disagree on the exact cut point for these terms, but by no more than +/−55.6° C. preferably no more than +/−27.8° C. Vacuum resid is the bottoms product from a distillation column operated under vacuum where the heaviest distilled product can be nominally 566° C., and is referred to as 566° C. resid. The cut point can be measured according to ASTM D1160-18.

The term "olefin product", as used herein, means a product that includes one or more olefins, preferably a product consisting essentially of one or more olefins. An olefin product in the meaning of this disclosure can be, e.g., an ethylene stream, a propylene stream, a butylene stream, an ethylene/propylene mixed stream, and the like.

The term "aromatic" as used herein is to be understood in accordance with its art-recognized scope which includes alkyl substituted and unsubstituted mono- and polynuclear compounds.

The term "consisting essentially of" as used herein means the composition, feed, or effluent comprises a given component at a concentration of at least 60 wt %, preferably at least 70 wt %, more preferably at least 80 wt %, more preferably at least 90 wt %, still more preferably at least 95 wt %, based on the total weight of the composition, feed, or effluent in question.

The term "rich" when used in phrases such as "X rich" or "rich in X" means, with respect to an outgoing stream obtained from a device, that the stream comprises material X at a concentration higher than in the feed material fed to the same device from which the stream is derived.

The term "lean" when used in phrases such as "X lean" or "lean in X" means, with respect to an outgoing stream obtained from a device, that the stream comprises material X at a concentration lower than in the feed material fed to the same device from which the stream is derived.

The terms "channel" and "line" are used interchangeably and mean any conduit configured or adapted for feeding, flowing, and/or discharging a gas, a liquid, and/or a fluidized solids feed into the conduit, through the conduit, and/or out of the conduit, respectively. For example, a composition can be fed into the conduit, flow through the conduit, and/or discharge from the conduit to move the composition from a first location to a second location. Suitable conduits can be or can include, but are not limited to, pipes, hoses, ducts, tubes, and the like.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All concentrations herein are expressed on the basis of the total amount of the composition in question. Thus, the concentrations of the various components of the "petroleum feed" are expressed based on the total weight of the petroleum feed. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, $6^{th}$ Edition, by F. Albert Cotton et al. (John Wiley & Sons, Inc., 1999).

The hydrocarbon-containing feed or simply the hydrocarbon feed can be, can include or can be derived from petroleum, plastic material, natural gas condensate, landfill gas (LFG), biogas, coal, biomass, bio-based oils, rubber, or any mixture thereof. In some examples, the hydrocarbon-containing feed can include a non-volatile component. In some examples, the petroleum can be or can include any crude or any mixture thereof, any crude fraction or any mixture thereof, or any mixture of any crude with any crude fraction. A typical crude includes a mixture of hydrocarbons with varying carbon numbers and boiling points. Thus, by using conventional atmospheric distillation and vacuum distillation, one can produce a range of fuel products with varying boiling points, e.g., naphtha, gasoline, kerosene, distillate, and tar. It is highly desired, however, to convert the large hydrocarbon molecules contained in the crude into more valuable, lighter products including but not limited to ethylene, propylene, butylenes, and the like, which can be further made into more valuable products such as polyethylene, polypropylene, ethylene-propylene copolymers, butyl rubbers, and the like.

In some examples, the petroleum can be or can include: crude oil, atmospheric resid, vacuum resid, steam cracked gas oil and residue, gas oil, heating oil, hydrocrackate, atmospheric pipestill bottoms, vacuum pipestill streams including bottoms, gas oil condensate, heavy non-virgin hydrocarbon stream from refineries, vacuum gas oil, heavy gas oil, naphtha contaminated with crude, heavy residue, C4's/residue admixture, naphtha/residue admixture, hydrocarbon gases/residue admixture, hydrogen/residue admixture, gas oil/residue admixture, or any mixture thereof. Non-limiting examples of crudes can be, or can include, but are not limited to, Tapis, Murban, Arab Light, Arab Medium, and/or Arab Heavy.

In some examples, the plastic material can be, or can include, but is not limited to, polyethylene terephthalate (PETE or PET), polyethylene (PE), polypropylene (PP), polyvinyl chloride (PVC), polyvinylidene chloride (PVDC), polystyrene (PS), polycarbonate (PC), polylactic acid (PLA), acrylic (PMMA), acetal (polyoxymethylene, POM), acrylonitrile-butadiene-styrene (ABS), fiberglass, nylon (polyamides, PA), polyester (PES) rayon, polyoxybenzylmethylenglycolanhydride (bakelite), polyurethane (PU), polyepoxide (epoxy), or any mixture thereof. The rubber can be or can include natural rubber, synthetic rubber, or a mixture thereof. In some examples, the biogas can be produced via anaerobic digestion, e.g., the biogas produced during the anaerobic digestion of sewage. In some examples, the biobased oil can be or can include oils that can degrade biologically over time. In some examples, the biobased oil can be degraded via processes of bacterial decomposition and/or by the enzymatic biodegradation of other living organisms such as yeast, protozoans, and/or fungi. Biobased oils can be derived from vegetable oils, e.g., rapeseed oil, castor oil, palm oil, soybean oil, sunflower oil, corn oil, hemp oil, or chemically synthesized esters. In some examples, the biomass can be or can include, but is not limited to, wood, agricultural residues such as straw, stover, cane trash, and green agricultural wastes, agro-industrial wastes such as sugarcane bagasse and rice husk, animal wastes such as cow manure and poultry litter, industrial waste such as black liquor from paper manufacturing, sewage, municipal solid waste, food processing waste, or any mixture thereof.

If the hydrocarbon-containing feed includes material that is solid at room temperature, e.g., plastic material, biomass, coal, and/or rubber, the solid material can be reduced to any desired particle size via well-known processes. For example, if the hydrocarbon-containing feed includes solid material, the solid material can be ground, crushed, pulverized, other otherwise reduced into particles that have any desired average particle size. In some examples, the solid matter can be reduced to an average particle size that can be submicron or from about 1 μm, about 10 μm or about 50 μm to about 100 μm, about 150 μm, or about 200 μm. For example, the average particle size of the solid material can range from about 75 μm to about 475 μm, from about 125 μm to about 425 μm, or about 175 μm to about 375 μm.

In some examples, the hydrocarbon-containing feed can include one or more crude oils or a fraction thereof and one or more plastic materials. In some examples, the hydrocarbon-containing feed can include petroleum and one or more plastic materials, the one or more plastic materials present in an amount in a range of from 1 wt %, 3 wt %, 5 wt %, 7 wt %, 10 wt %, or 15 wt % to 20 wt %, 25 wt %, 30 wt %, 35 wt %, 40 wt %, or 45 wt %, based on the total weight of the hydrocarbon-containing feed.

The petroleum, e.g., crude oil or fraction thereof, can act as a solvent for the plastic material and cause at least a portion of the plastic material to dissolve in the crude oil or fraction thereof. In some examples, at least 30 wt %, at least 40 wt %, at least 50 wt %, at least 60 wt %, at least 70 wt %, at least 80 wt %, at least 90 wt %, or even 100 wt % of the plastic material mixed with the crude oil or fraction thereof can be solubilized in the crude oil or fraction thereof. As such, in some examples, when the hydrocarbon-containing feed includes one or more plastic materials, the hydrocarbon-containing feed can be in the form of a solution in which the plastic material is homogeneously dispersed in the crude oil or fraction thereof.

In some examples, one or more vapor-liquid separators, e.g., a vaporization drum or a flashing drum, can be used to separate a hydrocarbon-containing feed, e.g., a raw crude oil or a desalted crude oil, to obtain an overhead vapor effluent and a bottoms liquid effluent. The bottoms liquid effluent can have a cutoff point from 300° C. to 700° C., e.g., 310° C. to 550° C., as measured according to ASTM D1160-18. The hydrocarbon-containing feed can be or can be obtained from the bottoms liquid effluent. In this example, at least a portion of the overhead vapor effluent can optionally be fed into another processing unit, e.g., a radiant section of a steam cracker furnace, a fluid catalytic cracker, other systems capable of upgrading the overhead vapor effluent, or any combination thereof. Suitable vaporization drums or flashing drums can include those disclosed in U.S. Pat. Nos. 7,674,366; 7,718,049; 7,993,435; 8,105,479; and 9,777,227. In some examples, if an overhead vapor and a liquid bottoms is separated from a hydrocarbon feed, the overhead vapor can be steam cracked according to the processes and systems disclosed in U.S. Pat. Nos. 6,419,885; 7,993,435; 9,637,694; and 9,777,227; U.S. Patent Application Publication No. 2018/0170832; and International Patent Application Publication No. WO 2018/111574.

Overview

Processes and systems for the production of a pyrolysis effluent that can include one or more olefins and a gasification zone effluent that can include a synthesis gas via the integration of one or more pyrolysis reactors and one or more gasifiers are disclosed. A hydrocarbon-containing feed and a plurality of heated particles can be introduced or otherwise fed into a pyrolysis reaction zone or simply pyrolysis zone disposed within the pyrolysis reactor and contacted therein to effect pyrolysis of at least a portion of the hydrocarbon-containing feed to produce a pyrolysis zone effluent that can include olefins and the particles having coke formed on the surface thereof. A first gaseous hydrocarbon stream rich in the olefins and a first particle stream rich in the particles can be obtained from the pyrolysis zone effluent. At least a portion of the first particle stream, an oxidant stream, a steam stream, and, optionally, a hydrocarbon fuel stream can be introduced or otherwise fed into a gasification zone disposed within the gasifier and contacted therein to effect gasification of at least a portion of the coke on the surface of the particles to produce a gasification zone effluent that can include heated and regenerated particles and a synthesis gas. The synthesis gas can include molecular hydrogen, carbon monoxide, and carbon dioxide. A second gaseous hydrocarbon stream rich in the synthesis gas and a second particle stream rich in the heated and regenerated particles can be separated or otherwise obtained from the gasification zone effluent. At least a portion of the second particle stream can be recycled back to the pyrolysis zone as at least a portion of the heated particles fed into the pyrolysis zone. The second particle stream can provide at least a portion of the heat required to effect pyrolysis of the hydrocarbon-containing feed within the pyrolysis zone.

In some examples, the integration of the pyrolysis reactor and the gasifier can allow for the production of a synthesis gas having a composition useful in producing a molecular hydrogen rich gas and/or chemicals, such as ammonia, urea, and/or methanol. One option that can be used to adjust the composition of the synthesis gas can be to reduce a molecular nitrogen content within the gasifier, such as by using an oxidant that contains molecular oxygen having a lower nitrogen content than air. Another option that can be used to improve the quality of the synthesis gas can be to introduce additional feeds, e.g., a hydrocarbon fuel, into the gasification zone that can be combusted and/or reformed, e.g., steam reformed, therein to produce additional synthesis gas.

In some examples, the integration can also provide for improved carbon capture, e.g., the capture of carbon dioxide during the synthesis of ammonia and/or urea. The carbon dioxide can be introduced or otherwise fed into a storage location for sequestration, used for enhanced oil recovery, and/or converted into other compounds. In some examples, 10 wt %, 15 wt %, or 20 wt % to about 30 wt %, 40 wt %, or 45 wt % of a total carbon content in the hydrocarbon containing feed can be converted into carbon dioxide in the process disclosed herein and the carbon dioxide can be utilized in an enhanced oil recovery process, sequestered, converted into another compound, or otherwise contained rather than being emitted into the environment.

In some examples, the integration can allow for reduced or minimized production of inorganic nitrogen compounds by using molecular oxygen, e.g., oxygen obtained from an air separation unit, as the oxidant introduced into the gasification zone. Although the amount of nitrogen introduced as a diluent into the gasification can be reduced or minimized, the integrated process can also allow for gasification of coke while reducing, minimizing, or eliminating the production of slag or other glass-like substances in the gasifier. This can be achieved, for example, by recycling a portion of the second gaseous stream rich in the synthesis gas and/or carbon dioxide separated therefrom back to the gasifier. In other examples, other diluent compounds such as steam, hydrocarbons, carbon monoxide, and/or inorganic compounds (such hydrogen sulfide and/or other inorganic compounds that are non-reactive in the gasifier environment) can be used as well.

The integration of the pyrolysis reactor and the gasifier with the production of a molecular hydrogen rich gas and/or with the production of one or more chemicals, e.g., ammonia, urea, and/or methanol production, can also provide advantages related to reduced plant's footprint and a significant reduction in capital costs. For example, when the synthesis gas is converted to ammonia, steam reforming reactions can be carried out in the gasifier, which can eliminate the need for a separate steam methane reforming unit to produce molecular hydrogen. Another advantage can include the elimination of a demethanator. Similar advantages in terms of equipment footprint reduction can be achieved for configurations that produce other chemicals such as urea and/or methanol.

Gasification

The first particle stream separated from the pyrolysis zone effluent, the steam stream, and the oxidant stream and, optionally, the hydrocarbon fuel stream can be introduced or otherwise fed into the gasification zone and can be converted to produce the synthesis gas via one or more reactions. The reactions that can occur within the gasification zone can include, but are not limited to, combustion ($C+O_2\rightarrow CO_2$), gasification ($C+H_2O\rightarrow CO+H_2$; $C+CO_2\rightarrow 2CO$); and/or water gas shift reaction ($CO+H_2O\leftrightarrow CO_2+H_2$). Suitable hydrocarbon fuel streams can be or can include, but are not limited to, methane, ethane, propane, natural gas, a fuel gas such as a mixture of one or more $C_1$-$C_5$ hydrocarbons, resid, pyrolysis tar, or any mixture thereof.

In some examples, the hydrocarbon fuel stream, when used, can be distributed in a relatively even manner in at least one radial zone, such as a middle radial zone of the gasifier, and the oxidant stream and the first particle stream can be fed into a different zone, such as a lower radial zone for an upflow type gasifier. This can facilitate combustion of at least a portion of the coke on the surface of the particles with the oxidant within the lower radial zone, thus allowing more of the hydrocarbon fuel to be converted via steam reforming in the middle or higher radial zone. Said another way, in some examples, the hydrocarbon fuel stream can be introduced into the gasification zone at a location downstream of where the oxidant stream and the first particle stream can be introduced into the gasification zone. It should be understood that if the hydrocarbon fuel and the particles having the coke disposed on the surface thereof are introduced into the same radial zone then the amount of the hydrocarbon fuel converted via steam reforming can be less since more of the oxidant would be available to combust the hydrocarbon fuel in the middle or upper radial zone. As such, the introduction of the hydrocarbon fuel, particles, and oxidant relative to one another can be used as a process control variable to further adjust the composition of the synthesis gas produced within the gasification zone.

In some examples, the gasification zone within the gasifier can be operated at a minimum temperature of at least 1,000° C., at least 1,050° C., at least 1,100° C., at least 1,150° C., at least 1,200° C., at least 1,250° C., or at least 1,300° C. to 1,350° C., 1,400° C., 1,450° C., or 1,500° C. The gasification zone can be operated at a pressure of 100 kPa-gauge, 200 kPa-gauge, 300 kPa-gauge, 400 kPa-gauge, or 500 kPa-gauge to 700 kPa-gauge, 800 kPa-gauge, 900 kPa-gauge, or 1,000 kPa-gauge. Operating the gasification zone at such an elevated temperature can produce heated and regenerated particles having a sufficient amount of heat that can be utilized within the pyrolysis zone to effect the pyrolysis of the hydrocarbon-containing feed, e.g., crude oil or a fraction thereof, which contains resid.

The amount of oxidant introduced into the gasification zone can be reduced or limited to a substoichiometric amount that would be needed for complete combustion of all the coke disposed on the particles and, if present, all of the hydrocarbon fuel introduced into the gasification zone. The amount of oxidant introduced into the gasification zone can be sufficient to combust a sufficient amount of the coke and, if present, optionally combust a sufficient amount of the hydrocarbon fuel to provide heat for the gasification zone and at least a portion of the heat within the pyrolysis zone via the heated and regenerated particles recycled thereto. In some examples, the amount of oxidant introduced into the gasification zone can be 30% to 90% or 50% to 70% of the amount of oxidant that would be required for complete combustion of all the coke formed on the surface of the particles and, if present, all of the hydrocarbon fuel introduced into the gasification zone.

In some examples, the oxidant stream can be a molecular oxygen containing gas that can have a low nitrogen content, such as oxygen from an air separation unit or another oxygen stream. In some examples, an oxidant stream that can include 40 vol %, 50 vol %, 60 vol %, 70 vol %, 80 vol %, 90 vol %, 95 vol %, 98 vol % or more of molecular oxygen and a nitrogen rich stream can be separated from air and the oxidant stream that includes 40 vol % or more of molecular oxygen can be introduced into the gasification zone. The second gaseous stream separated from the gasification zone effluent can have a reduced amount of nitrogen as compared to if air were used as the oxidant and the nitrogen rich stream can be used as a nitrogen source in the production of ammonia.

If an oxidant having a low nitrogen content is used, in some examples a separate diluent stream, such as a recycled second gaseous stream or a recycled carbon dioxide rich stream separated from the second gaseous stream obtained from the gasification zone effluent can also be fed into the gasifier. In some examples, the diluent stream, if used, can include 5 vol % or 10 vol % to 15 vol % or 20 vol % of the second gaseous stream obtained from the gasification zone effluent. In other examples, the diluent stream can include 5 vol % or 10 vol % to 15 vol % or 20 vol % of the compressed second gaseous stream obtained from the gasification zone effluent.

Alternatively, if a sufficient amount of hydrocarbon fuel stream and/or steam stream are introduced into the gasification zone, the hydrocarbon fuel stream and/or the steam stream can serve as the additional diluent. If at least a portion of the diluent is selected based on a consideration other than facilitating the reforming reaction in the gasifier, the amount of diluent can be selected by any convenient method. For example, the amount of diluent can be selected so that the amount of diluent replaces the weight of molecular nitrogen that would be present in the oxidant stream if air was used as the oxidant. In another example, the amount of diluent can be selected to allow for replacement of the same BTU value for heat removal that would be available if molecular nitrogen was present based on the use of air as the oxidant.

In other examples, the oxidant stream introduced into the gasification zone can include an amount of molecular nitrogen sufficient to allow a portion of the gasification zone effluent to be used as an input for ammonia synthesis. In this example, sufficient reforming can be performed so that a molar ratio of molecular hydrogen to molecular nitrogen in the second gaseous hydrocarbon obtained from the gasification zone effluent can be 1.5 or more, e.g., 1.5:1, 1.75:1, or 2:1 to 2.3:1, 2.5:1, or 2.7:1. In such examples, some options for increasing the molecular hydrogen content of the second gaseous stream can include performing steam reforming in the gasifier and adding excess steam to assist with shifting carbon monoxide to carbon dioxide, thereby producing molecular hydrogen via the water gas shift reaction. In such examples, an air separation unit can be used to produce an oxidant stream with a reduced amount of molecular nitrogen. As such, the amount of molecular nitrogen in the oxidant can be any convenient amount that assists with achieving a desired ratio of molecular hydrogen to molecular nitrogen in the second gaseous hydrocarbon stream.

In some examples, the oxidant stream can include air or a fraction of air. In such example, on a volume basis, a total amount of molecular oxygen to a total amount of molecular nitrogen within the oxidant stream and within the gasification zone can be at least 0.26:1, e.g., 0.3:1 or 0.4:1.

The amount of steam introduced into the gasification zone can be sufficient to promote the water conversion to molecular hydrogen along with carbon monoxide or carbon dioxide. This can assist with producing a more desirable ratio of molecular hydrogen to carbon monoxide in the synthesis gas. In some examples, the molar amount of steam introduced into the gasification zone can be 0.1 to 10, based on carbon introduced into the gasifier. In some examples, the molar amount of the hydrocarbon fuel, if introduced into the gasification zone, can be 0.1 to 10, based on carbon in coke introduced to the gasifier. The particular rate or amount of steam, oxidant, hydrocarbon fuel, and any diluent stream introduced into the gasification zone can depend, at least in part, on the rate or amount that the coke formed on the surface of the particles enters from the pyrolysis zone and to a lesser extent upon the composition of the coke which, in turn can vary based, at least in part, on the composition of the hydrocarbon-containing feed and the severity of the pyrolysis conditions in the pyrolysis zone.

In some examples, 97 wt % or 98 wt % to 99 wt % or 100 wt % of a carbon content of the hydrocarbon fuel stream can be converted into carbon monoxide, carbon dioxide, or both within the gasification zone. In some examples, 85 wt % or 90 wt % to 95 wt % or 99 wt % of a carbon content of the coke disposed on the particles can be converted into carbon monoxide, carbon dioxide, or both within the gasification zone. In some examples, 50 wt %, 60 wt %, 70 wt %, or 80 wt % to 85 wt %, 90 wt %, 95 wt %, or 100 wt % of the hydrocarbon fuel stream can be combusted within the gasification zone. In some examples, 70 wt %, or 80 wt % to 85 wt %, 90 wt %, 95 wt %, or 100 wt % of the coke on the surface of the particles can be combusted within the gasification zone.

The gasification zone can be located in any suitable reactor or other process environment capable of operating under the gasification process conditions. In some examples, the gasification zone can be located in short contact time fluidized bed reactor. In some examples, the gasification zone can be located in a downflow reactor, an upflow reactor, or a counter-current flow reactor. In a preferred example, the gasification zone can be located in a downflow reactor. In another preferred example, the gasification zone can be located in an upflow reactor including a fixed fluid bed.

In some examples, the second gaseous steam can include 10 wt %, 13 wt %, or 15 wt % to 17 wt %, 20 wt %, 25 wt %, or 30 wt % of molecular hydrogen, based on a total weight of the second gaseous stream. In some examples, the second gaseous stream can include 12 wt %, 15 wt %, 17 wt %, or 20 wt % to 25 wt %, 27 wt %, 30 wt %, 33 wt %, or 35 wt % of carbon monoxide, based on the total weight of the second gaseous stream. In some examples, the second gaseous stream can include 5 wt %, 7 wt %, 10 wt %, or 12 wt % to 15 wt %, 17 wt %, or 20 wt % of carbon dioxide, based on the total weight of the second gaseous stream. In some examples, the second gaseous stream can include 10 wt % to 20 wt %% of molecular hydrogen, 15 wt % to 25 wt % of carbon monoxide, and 5 wt % to 15 wt % or carbon dioxide, based on the total weight of the second gaseous stream. In other examples, the second gaseous stream can include 10 wt % to 25 wt % of molecular hydrogen, 15 wt % to 30 wt % of carbon monoxide, and at least 5 wt % of carbon dioxide, based on the total weight of the second gaseous stream. It should be understood, that if a diluent that is or includes carbon dioxide is introduced into the gasification zone, the amount of carbon dioxide in the synthesis gas can be significantly greater than 20 wt %.

Processing the Gasification Zone Effluent

The gasification zone effluent can be separated to provide the heated and regenerated particles and the second gaseous stream rich in the synthesis gas. In some examples, the gasification zone effluent can be introduced or otherwise fed into a first separation vessel that can include an inertial separator configured to separate a majority of the heated and regenerated particles from the gaseous components to produce the second gaseous stream and the second particle stream rich in the heated and regenerated particles. Inertial separators can be configured or adapted to concentrate or collect the particles by changing a direction of motion of the pyrolysis effluent such that the particle trajectories cross over the hydrocarbon gas streamlines and the particles are either concentrated into a small part of the gas flow or are separated by impingement onto a surface. In some examples, a suitable inertial separator can include a cyclone. The gasification zone effluent, when introduced into a cyclone can undergo a vortex motion so that the hydrocarbon gas acceleration is centripetal and the particles, therefore, move centrifugally towards the outside of the cyclone, i.e., an inner surface of the cyclone. Illustrative cyclones can include, but are not limited to, those disclosed in U.S. Pat. Nos. 7,090,081; 7,309,383; and 9,358,516.

In some examples, the second gaseous stream rich in the synthesis gas obtained from the gasification zone effluent can contain entrained coke solids that can be removed via one or more cyclones, via a condensate produced by cooling the synthesis gas to condense the steam, and/or any other suitable separation techniques. In some examples, cyclones, if used, can be internal cyclones in the main gasifier vessel itself or external in a separate, smaller vessel. Other separation devices such as sintered metal filters can also be used.

In some examples, the second gaseous stream can be introduced into one or more indirect heat exchange stages that can be configured to transfer heat from the second gaseous stream to a cooling medium, e.g., water, to produce a cooled second gaseous steam that can include water. The cooled second gaseous stream can be introduced into a separation stage that can separate at least a portion of the water and, if present, entrained particles with the water to produce a relatively dried second gaseous stream.

In some examples, the synthesis gas can include hydrogen sulfide. If the synthesis gas includes hydrogen sulfide, at least a portion of the hydrogen sulfide can be removed to produce a purified second gaseous stream. Any convenient method for removal of hydrogen sulfide can be used. In examples, where an amine wash is used for carbon dioxide separation, the amine wash can also be effective for hydrogen sulfide removal. In some examples, the hydrogen sulfide can be removed in an adsorbent stage, such as a Flexsorb® sulfur removal stage. In some examples, the sulfur removal stage can be selective for the removal of sulfur, e.g., hydrogen sulfide, while reducing or minimizing removal of carbon dioxide.

The purified second gaseous stream can be compressed to produce a compressed gaseous stream. The compression of the purified second gaseous stream can be compressed via one or more compressors that can also be used to compress one or more hydrocarbon products recovered or otherwise obtained from the pyrolysis reaction zone effluent. The compressed second gaseous stream can be introduced into a water gas shift stage to convert at least a portion of the carbon monoxide to carbon dioxide to produce a shifted synthesis gas stream.

The shifted synthesis gas stream can be introduced or otherwise fed into one or more carbon dioxide separation stages to produce a carbon dioxide lean synthesis gas stream and a carbon dioxide rich stream. Any convenient type of carbon dioxide separation can be used, such as cryogenic separation, membrane separation, and/or adsorption (including swing adsorption). The resulting high purity carbon dioxide stream can be sequestered. Optionally, at least a portion of the carbon dioxide can be used for chemical production and/or enhanced oil recovery.

In some examples, the second gaseous stream and the carbon dioxide lean synthesis gas stream obtained therefrom can include molecular nitrogen. In such example, on a volume basis, second gaseous stream and the synthesis gas can include a greater amount of molecular hydrogen than molecular nitrogen.

The carbon dioxide lean synthesis gas stream can be further used to produce one or more chemicals as further described below.

Pyrolysis Reactor

The hydrocarbon-containing feed and a plurality of heated particles can be introduced or otherwise fed into the pyrolysis reaction zone or simply the pyrolysis zone. In some examples, the hydrocarbon-containing feed can be heated, e.g., via indirect heat exchange with a heated medium, to a temperature in a range from 100° C., 150° C., or 200° C. to 300° C., 350° C., or 400° C., e.g., 250° C. to 300° C., prior to feeding the hydrocarbon-containing feed into the pyrolysis zone.

In some examples, the heated and regenerated particles can be obtained from the gasification zone effluent and introduced directly into the pyrolysis zone. In other examples, the heated and regenerated particles can optionally be further heated, e.g., in a combustion zone, before feeding at least a portion of the regenerated particles into the pyrolysis zone. If regenerated particles are substantially free of any coke, in addition to an oxidant, e.g., molecular oxygen, a hydrocarbon fuel can be combusted to further heat the regenerated particles. In some examples, the heated particles introduced into the pyrolysis zone can be entirely derived from the second particle stream rich in the heated and regenerated particles.

The hydrocarbon-containing feed can contact the plurality of heated particles in the pyrolysis zone to effect pyrolysis of at least a portion of the hydrocarbon-containing feed or fraction thereof to produce a pyrolysis zone effluent. The plurality of heated particles can be at a temperature of 800° C., 850° C., 900° C., or 950° C. to 1,050° C., 1,100° C., 1,200° C., 1,300° C., 1,400° C., or 1,500° C. when fed into the pyrolysis zone. In some examples, the plurality of heated particles can be at a temperature of at least 800° C., at least 820° C., at least 840° C., at least 850° C., at least 875° C., at least 900° C., at least 950° C., or at least 975° C. to 1,000° C., 1,025° C., 1,050° C., 1,075° C., 1,100° C., or 1,150° C.

The pyrolysis zone effluent can include, but is not limited to, the particles having coke formed on the surface thereof and olefins, e.g., alkenes such as ethylene and propylene, aromatics such as benzene, toluene, and/or xylene, molecular hydrogen ($H_2$), or any mixture thereof. The first hydrocarbon stream rich in olefins obtained from the pyrolysis zone effluent can include a relatively high percentage of olefins. In some examples, the first gaseous hydrocarbon stream rich in the olefins can include 15 wt %, 17 wt %, 20 wt, 23 wt %, or 25 wt % to 27 wt %, 30 wt %, 40 wt %, 50 wt %, 60 wt %, or 70 wt % of olefins, based on a total weight of the first gaseous hydrocarbon stream. The olefins in the first hydrocarbon stream can include a relatively high percentage of ethylene and/or propylene. In some examples, the combined amount of any ethylene and any propylene can be 60 wt %, 65 wt %, 70 wt %, or 75 wt % to 80 wt %, 85 wt %, 90 wt %, 95 wt % or more, based on a combined weight of all olefins in the first gaseous hydrocarbon stream rich in the olefins.

In some examples, the particles can be brought into contact with the hydrocarbon-containing feed at a negative velocity or at low or no velocity with the hydrocarbon-containing feed at a substantially higher velocity, to entrain the particles in the hydrocarbon-containing feed, transfer heat from the particles to the hydrocarbon-containing feed and crack the same. As the particles pass through the pyrolysis zone, the particles can accelerate, but the pyrolysis of the hydrocarbon-containing feed can be terminated or substantially terminated before the particles attain the velocity of the gas, e.g., the particles can be separated from pyrolysis effluent while the solids are substantially below the velocity of the gaseous components and the gaseous components can be quenched. As used herein, the phrase "negative velocity" means that the particles are thrown into the reactor in a direction away from the direction of the gaseous component flow and are then carried by the gaseous components in the direction of the gaseous component flow.

In some examples, the plurality of fluidized particles can include an oxide of a transition metal element capable of oxidizing molecular hydrogen ($H_2$) at the first temperature. At least a portion of the transition metal element disposed on and/or in the particles in the pyrolysis effluent can be at a reduced state as compared to the transition metal element in the plurality of fluidized particles fed into the pyrolysis reaction zone.

The hydrocarbon-containing feed can be contacted with an amount of the plurality of fluidized particles within the pyrolysis reaction zone sufficient to effect a desired level or degree of pyrolysis of the hydrocarbon-containing feed. In some examples, a weight ratio of the plurality of fluidized particles to the hydrocarbon-containing feed when contacted within the pyrolysis reaction zone can be 5:1, 10:1, 12:1, 15:1, or 20:1 to 25:1, 30:1, 35:1, 40:1, 45:1, 50:1, 55:1, or 60:1.

The pyrolysis reaction zone can be located in any suitable reactor or other process environment capable of operating under the pyrolysis process conditions. In some examples, the pyrolysis reaction zone can be located in short contact time fluid bed. In some examples, the pyrolysis reaction zone can be located in a downflow reactor, an upflow reactor, a counter-current flow reactor, or vortex reactor. In a preferred example, the pyrolysis reaction zone can be located in a downflow reactor.

In some examples, the hydrocarbon-containing feed can be contacted with the plurality of fluidized particles in the pyrolysis reaction zone in the presence of steam. The steam, if used, can be introduced or otherwise fed into the pyrolysis reaction zone in an amount sufficient to provide a weight ratio of the steam to the hydrocarbon-containing feed of 0.01:, 0.05:1, 0.1:1, 0.5:1, or 0.7:1 to 1:1, 2:1, 3:1, 4:1, 5:1, or 6:1. In other examples, the steam can be introduced or otherwise fed into the pyrolysis reaction zone in an amount sufficient to provide a weight ratio of the steam to the hydrocarbon-containing feed of 0.05:1, 0.1:1, 0.2:1, 0.25:1, 0.3:1, or 0.4:1 to 0.5:1, 0.6:1, 0.7:1, 0.8:1, 0.9:1, or 1:1. For example, the weight ratio of the steam to the hydrocarbon-containing feed can be about 0.2:1 to about 0.6:1 or about 0.3:1 to about 0.5:1.

The hydrocarbon-containing feed can contact the plurality of fluidized particles within the pyrolysis reaction zone under a vacuum, at atmospheric pressure, or at a pressure greater than atmospheric pressure. In some examples, the hydrocarbon-containing feed can contact the plurality of fluidized particles within the pyrolysis reaction zone under an absolute pressure of 101 kPa, 150 kPa, 200 kPa, 250 kPa, 300 kPa, or 400 kPa to 450 kPa, 500 kPa, 550 kPa, 600 kPa, 650 kPa, 700 kPa, 750 kPa, 800 kPa, 850 kPa, 900 kPa, 950 kPa, or 1,000 kPa. In some examples, the hydrocarbon-containing feed can contact the plurality of fluidized particles within the pyrolysis reaction zone under an absolute pressure of 101 kPa to 800 kPa, 101 kPa to 700 kPa, 101 kPa to 500 kPa, 200 kPa to 800 kPa, 220 kPa to 460 kPa, or 101 kPa to 450 kPa. In other examples, the hydrocarbon-containing feed can contact the plurality of fluidized particles within the pyrolysis reaction zone under an absolute pressure of less than 800 kPa, less than 700 kPa, less than 600 kPa, less than 500 kPa, less than 450 kPa, less than 400 kPa, less than 350 kPa, less than 300 kPa, less than 250 kPa, less than 200 kPa, or less than 150 kPa.

The hydrocarbon-containing feed can contact the plurality of fluidized particles within the pyrolysis reaction zone for a residence time of 1 millisecond (ms), 5 ms, 10 ms, 25 ms, 50 ms, 75 ms, or 100 ms to 300 ms, 500 ms, 700 ms, 1,000 ms, 1,250 ms, 1,500 ms, 1,750 ms, or 2,000 ms. In some examples, the hydrocarbon-containing feed can contact the plurality of fluidized particles within the pyrolysis reaction zone for a residence time of 10 ms to 500 ms, 10 ms to 100 ms, 20 ms to 200 ms, 30 ms to 225 ms, 50 ms to 250 ms, 125 ms to 500 ms, 200 ms to 600 ms, or 20 ms to 140 ms. In other examples, the hydrocarbon-containing feed can contact the plurality of fluidized particles within the pyrolysis reaction zone for a residence time of less than 1,000 ms, less than 800 ms, less than 600 ms, less than 400 ms, less than 300 ms, less than 200 ms, less than 150 ms, or less than 100 ms.

Without wishing to be bound by theory, it is believed that when the particles include the optional oxide of the transition metal element capable of oxidizing molecular hydrogen at the first temperature can do so via one or more processes or mechanisms. Regardless of the overall mechanism, the oxidized transition metal element can facilitate the conversion of molecular hydrogen to water and in doing so the oxidation state of the oxide of the transition metal element can be reduced. For example, if the transition metal element is vanadium, the oxide of vanadium on the fluidized particles fed into the pyrolysis reaction zone can be at an oxidation state of +5 (for example) and at least a portion of the oxide of vanadium on the fluidized particles in the pyrolysis effluent can be at an oxidation state of +4, +3, or +2. Without wishing to be bound by theory, it is also believed that one or more of the oxides of one or more transition metal elements may be capable of being reduced from an oxidized state all the way to the metallic state.

Additionally, the oxide of the transition metal element, if present, can favor the conversion, e.g., oxidation and/or combustion, of hydrogen over the oxidation and/or combustion of hydrocarbons, e.g., olefins, in the pyrolysis reaction zone. In some examples, the oxide of the transition metal element can favor the conversion of hydrogen over the conversion of hydrocarbons at a rate of 2:1, 3:1, 4:1, 5:1, 6:1, or 7:1 to 8:1, 9:1, 10:1, or 11:1.

In some examples, the presence of the oxide of the transition metal in the fluidized particles, e.g., disposed on an outer surface of the particles and/or at least partially within the particles, can reduce an amount of molecular hydrogen present in the pyrolysis effluent as compared to a comparative pyrolysis effluent produced under the same process conditions and with the same fluidized particles except the oxide of the transition metal is absent. As such, in some examples, it can be desirable to use particles having the transition metal element disposed on the surface thereof and, in other examples, it can be desirable to use particles without the transition metal element disposed on the surface thereof.

In some examples, during contact of the hydrocarbon-containing feed with the plurality of fluidized particles in the pyrolysis reaction zone, the coke can be formed on the surface of the particles. For example, when the hydrocarbon-containing feed includes non-volatile components at least a portion of the non-volatile components can deposit, condense, adhere, or otherwise become disposed on the surface of the particles and/or at least partially within the particles, e.g., within pores of the particles, in the form of coke. As such, the pyrolysis effluent can include the particles in which at least a portion of the transition metal element can be at a reduced state and at least a portion of the particles can include coke formed or otherwise disposed on the surface thereof and/or at least partially therein. In some examples, the particles in the pyrolysis effluent can include 1 wt %, 3 wt %, 5 wt %, 7 wt %, 10 wt %, or 15 wt % to 20 wt %, 25 wt %, 30 wt %, 35 wt %, 40 wt %, 45 wt %, or 50 wt % of coke, based on a total weight of the particles.

Fluidized Particles

In some examples, the particles can be or can include a core. In other examples, the particles can be or include a core and at least one transition metal element and/or at least one oxidized transition metal element disposed on and/or in the core. In some examples, the core can be inert, i.e., inert during pyrolysis of the hydrocarbon-containing feed. The core can be or can include, but is not limited to, silica, alumina, titania, zirconia, magnesia, pumice, ash, clay, diatomaceous earth, bauxite, or any mixture or combination thereof. In some examples, the core can be or can include spent fluidized catalytic cracker catalyst, where the spent catalyst is inert or substantially inert during pyrolysis of the hydrocarbon containing feed. Preferred support materials can be or can include $Al_2O_3$, $ZrO_2$, $SiO_2$, and combinations thereof, more preferably, $SiO_2$, $Al_2O_3$, or $SiO_2/Al_2O_3$. In other examples, the particles can be free or substantially free of any transition metal element. In some examples, during contact of the particles with the hydrocarbon-containing feed, one or more transition metal elements can be deposited on the surface of the particles if the hydrocarbon-containing feed includes transition metal elements, e.g., a crude oil or a fraction thereof such as a resid.

In some examples, the transition metal element and/or the oxide thereof can be disposed on and/or within, e.g., within pores, of the core. In some examples, the transition metal element and/or the oxide thereof can form a surface layer on the core. The surface layer on the core can be continues or discontinuous.

The core and/or the particles that include the at least one transition metal element and/or at least one oxidized transition metal element disposed on and/or in the core can have an average size in a range from 10 micrometers (μ), 15 μm, 25 μm, 50 μm, or 75 μm to 150 μm, 200 μm, 300 μm, 400

µm. The core and/or the particles that include the at least one transition metal element and/or at least one oxidized transition metal element disposed on and/or in the core can have a surface area in a range from 10 m²/g, 50 m²/g, or 100 m²/g to 200 m²/g, 500 m²/g, or 700 m²/g.

In some examples, the fluidized particles can be, can include, or can otherwise be derived from spent fluid catalytic converter ("FCC") catalyst. As such, a significant and highly advantageous use for spent FCC catalyst has been discovered because the processes disclosed herein can significantly extend the useful life of FCC catalyst in upgrading hydrocarbons long after the FCC catalyst is considered to be spent and no longer useful in the fluid catalytic cracking process.

When the particles include the transition metal element, the plurality of fluidized particles can include any oxide of a transition metal element capable of converting at least a portion of any hydrogen to water, e.g., via oxidation, combustion, or other mechanism, within the pyrolysis reaction zone. In some examples, the transition metal element can be or can include, but is not limited to, titanium, vanadium, chromium, manganese, iron, cobalt, niobium, nickel, molybdenum, tantalum, tungsten, alloys thereof, and mixtures thereof. In some examples, the transition metal element can be or can include vanadium, nickel, an alloy thereof, or a mixture thereof.

The amount of transition metal element, when present, disposed on and/or at least partially within the plurality of fluidized particles can be in a range from 500 wppm, 750 wppm, 1,000 wppm, 2,500 wppm, 5,000 wppm, or 1 wt % to 2 wt %, 5 wt %, 10 wt %, 15 wt %, 20 wt %, 30 wt %, 40 wt %, or 50 wt %, based on a total weight of the particles. In some examples, the amount of transition metal element disposed on and/or at least partially within the plurality of fluidized particles can be at least 1 wt %, at least 2.5 wt %, at least 3 wt %, at least 3.5 wt %, at least 4 wt %, at least 4.5 wt %, at least 5 wt %, or at least 10 wt % up to 15 wt %, 20 wt %, 30 wt %, 40 wt %, or 50 wt %.

In some examples, the pyrolysis reactor, particles that include the transition metal element, process conditions, hydrocarbon feeds, hydrocarbon products, etc., can be or can include those described in U.S. Pat. No. 4,828,681; and U.S. Provisional Patent Application No. 62/882,218, filed on Aug. 2, 2019, and titled "Processes and Systems for Upgrading a Hydrocarbon-Containing Feed".

Ammonia Production

Ammonia can typically be made from molecular hydrogen and molecular nitrogen via the Haber-Bosch process at elevated temperature and pressure. Conventionally, the inputs can be a purified molecular hydrogen stream, which can be made from a multi-step process that can typically require steam methane reforming, water gas shift, water removal, and trace carbon oxide conversion to methane via methanation; and a purified molecular nitrogen stream, which can typically be derived from air via one or more air separation units. The air separation unit can be or can include, but is not limited to, a cryogenic air separation unit, a membrane separation unit, a pressure swing adsorption unit, a vacuum pressure swing adsorption unit, and/or any other device or system capable of separating oxygen and nitrogen from air.

In some examples, the purified molecular hydrogen for ammonia production can be provided from the carbon dioxide lean synthesis gas stream. As described above, the second gaseous stream rich in synthesis gas generated by the gasifier can be further processed to remove impurities such as sulfur to produce a carbon dioxide lean synthesis gas stream. For ammonia synthesis, the hydrogen stream can preferably be substantially free of impurities such as hydrogen sulfide. If a portion of the carbon dioxide lean synthesis gas produced in the gasifier is used as a source of hydrogen for ammonia synthesis, the synthesis gas can first be reacted in the water-gas shift reactor to increase the amount of molecular hydrogen relative to carbon monoxide. Following this, the gas can undergo separation via one or more processes to purify the molecular hydrogen stream. This can involve, for example, condensation of the water, removal of carbon dioxide, purification of the molecular hydrogen stream and then a final methanation step at elevated pressure (typically about 15 barg to about 30 barg, or about 1.5 MPag to about 3 MPag) to increase the amount of carbon oxide(s) that can be eliminated. The molecular hydrogen stream can be compressed to ammonia synthesis conditions of about 60 barg (about 6 MPag) to about 180 barg (about 18 MPag).

In some examples, the air separation unit that can optionally provide the oxidant stream for gasification can also produce a suitable nitrogen stream for use in making ammonia. The nitrogen stream can be combined with the molecular hydrogen stream to produce a mixture that can be exposed to the ammonia synthesis catalyst under ammonia synthesis conditions to produce ammonia. In some examples, a sufficient portion of molecular nitrogen can be left in the oxidant stream fed into the gasification zone so that the second gaseous stream rich in the synthesis gas feeding an ammonia plant can also contain a major portion of the molecular nitrogen needed for ammonia production.

Typical ammonia processes can be performed at about 350° C. to about 500° C., such as at about 450° C. or less, and can result in low conversion per pass (typically less than about 20%) and a large recycle stream. In some examples, a purge stream from the ammonia plant can be recycled to the gasifier for additional recovery of synthesis gas.

Urea Production

Urea is another large chemical product that can be made by the reaction of ammonia with carbon dioxide. The basic process is also referred to as the Bosch-Meiser urea process after its discoverers. The various urea processes can be characterized by the conditions under which urea formation takes place and the way in which unconverted reactants are further processed. The process includes two main equilibrium reactions, with incomplete conversion of the reactants. The net heat balance for the reactions can be exothermic. The first equilibrium reaction can be an exothermic reaction of liquid ammonia with dry ice (solid $CO_2$) to form ammonium carbamate ($H_2N$—$COONH_4$):

$$2NH_3 + CO_2 \leftrightarrow H_2N—COONH_4$$

The second equilibrium reaction can be an endothermic decomposition of ammonium carbamate into urea and water:

$$H_2N—COONH_4 \leftrightarrow (NH_2)_2CO + H_2O$$

The urea process can use liquefied ammonia and carbon dioxide at high pressure as process inputs. In prior art processes, carbon dioxide is typically provided from an external resource where it must be compressed to high pressure. In contrast, the current process can produce a high pressure carbon dioxide stream suitable for reaction with the liquid ammonia product from the ammonia synthesis reaction. It is noted that the gasification oxidant stream can be varied to adjust the amount of carbon dioxide produced. In addition, at least a portion of any carbon monoxide produced in the gasification zone and steam can be reacted to produce additional molecular hydrogen and carbon dioxide for use in producing additional ammonia that can lead to an increase in urea production.

In some examples, the urea process can be integrated into a combined system with an ammonia synthesis unit, the pyrolysis reactor, and the gasifier. This integrated approach can reduce and/or eliminate many processes from the conventional approach, which can require an ammonia plant (steam reformer, water gas shift, air separation unit to produce molecular hydrogen and an air separation plant) plus a separate supply of carbon dioxide typically made remotely and then transported to the plant. The current system can eliminate many of these processes, as well as providing carbon dioxide for use in forming the urea. Specifically, rather than transporting carbon dioxide as dry ice for use at a remote urea plant, carbon dioxide can be provided via separation of the synthesis gas stream obtained from the gasifier.

Methanol Production

During methanol synthesis, carbon monoxide and hydrogen can react over a catalyst to produce methanol. Commercial methanol synthesis catalysts can be highly selective, e.g., with a selectivity of greater than 99.8% possible under optimized reaction conditions. Typical reaction conditions can include pressures of about 5 MPa to about 10 MPa and temperatures of about 250° C. to about 300° C. With regard to the synthesis gas for methanol synthesis, the preferred ratio of molecular hydrogen to carbon monoxide of about 2:1 ($H_2$:CO) does not match the typical ratio generated by a gasifier. For example, a gasifier $H_2$:CO ratio is about 1:1. In some examples, production of methanol using carbon dioxide lean synthesis gas from the gasifier can be improved by addition of molecular hydrogen to the carbon dioxide lean synthesis gas stream. Additionally or alternately, catalysts that facilitate methanol formation from synthesis gas can sometimes additionally facilitate the water-gas shift reaction. As a result, the reaction scheme below shows that carbon dioxide can also be used to produce methanol:

$$2H_2+CO=>CH_3OH$$

$$3H_2+CO_2=>CH_3OH+H_2O$$

For methanol synthesis reactions, the composition of the synthesis gas can be characterized by the Module value M:

$$M=[H_2-CO_2]/[CO+CO_2]$$

Module values close to 2 can generally be suitable for production of methanol, such as values of M that are at least about 1.7, or at least about 1.8, or at least about 1.9, and/or less than about 2.3, or less than about 2.2, or less than about 2.1. As can be noted from the Module Value equation above, in addition to the ratio of molecular hydrogen to carbon monoxide, the ratio of carbon monoxide to carbon dioxide in the synthesis can impact the reaction rate of the methanol synthesis reaction.

The output stream from the gasifier can contain relatively high concentrations of molecular hydrogen, carbon monoxide, carbon dioxide, and water. Through a combination of separations, (reverse) water gas shift reactions, and/or other convenient mechanisms, the composition of the synthesis gas can be adjusted for us in the synthesis of methanol. In some examples the adjustment of the composition can include removing excess water and/or carbon dioxide, adjusting the ratio of molecular hydrogen to carbon monoxide, adjusting the Module value M, or any combination thereof. For example, a typical synthesis gas from the gasifier may have molecular hydrogen to carbon monoxide ratio of about 1:1. Removal of carbon dioxide from the synthesis gas can facilitate a subsequent water gas shift reaction to increase this ratio to closer to 2:1 and/or to increase the Module value M of the stream to closer to 2.

In a typical methanol plant, a large percentage of the reactor exhaust can be recycled after recovery of methanol liquid, due to low conversion per pass. In some configurations, the output from the methanol synthesis reaction can be separated into a liquid alcohol product, a recycle synthesis gas stream, and a vented purge gas. The vented purge gas can contain synthesis gas components, fuel components, e.g., methane, and inerts. In some aspects, at least a portion of the vented purge can be used to raise steam for heating in the synthesis gas production. Additionally or alternately, at least a portion of the purged gas can be upgraded to synthesis gas in the gasifier, e.g., introduced as at least a portion of the optional hydrocarbon fuel.

Example

The FIG. depicts an illustrative system 101 for processing a hydrocarbon-containing feed in line 1001, according to one or more embodiments. The system 101 can include one or more pyrolysis reactors 1007, one or more separation stages 1015, and one or more gasifiers 1027. The system 101 can also include one or more heat exchange stages 1045, one or more separation stages 1047, one or more hydrogen sulfide removal stages 1053, one or more compression stages 1059, one or more water gas shift stages 1069, and one or more carbon dioxide separation stages 1073. In some examples, the system 101 can include one or more urea synthesis units 1083, one or more ammonia synthesis units 1091, and/or one or more methanol synthesis units 1099. In some examples, the system 101 can also include one or more air separation units 1037.

The hydrocarbon-containing feed via line 1001 and heated and regenerated particles via line 1031 can be introduced or otherwise fed into the pyrolysis reactor 1007. In some examples, a plurality of heated particles via line 1003 can optionally be introduced into the pyrolysis reactor 1007. Feeding the heated particles via line 1003 into the pyrolysis reactor 1007 can be used during start-up of the pyrolysis reactor 1007 and/or to provide make-up or replacement particles as some of the particles can be removed from the system 101 via line 1021. In some examples, steam via line 1005 can also be introduced into the pyrolysis reactor 1007.

The hydrocarbon-containing feed and optionally the steam can contact the plurality of heated particles within a pyrolysis zone 1009 of the pyrolysis reactor 1007 to effect pyrolysis of at least a portion of the hydrocarbon-containing feed to produce a pyrolysis zone effluent. The pyrolysis zone effluent can include olefins and particles having coke deposited or otherwise formed on a surface thereof. The velocity of the gaseous components within the pyrolysis zone 1009 can be maintained at a velocity of at least 20% greater than a velocity of the particles within the pyrolysis zone 1009.

The pyrolysis zone effluent via line 1011 can be introduced into the separation stage, e.g., separation device or separation vessel, 1015 that can be adapted or configured to receive the pyrolysis zone effluent. Optionally a stripping steam stream via line 1013 can be introduced into the separation vessel 1015 to improve the separation of gaseous components that can be entrained in the particles. A first gaseous stream rich in the olefins via line 1017 and a first particle stream rich in the particles via channel or line 1019 can be discharged or otherwise obtained from the separation vessel 1015.

At least a portion of the first particle stream via line 1019 can be introduced or otherwise fed into the gasifier 1027. In some examples, a portion of the particles within the separation vessel 1015 can be removed via line 1021 from the system 101. In some examples, it can be desirable to remove some of the particles via line 1021 and replace the removed particles with fresh or make-up particles via line 1003. For example, should the particles accumulate too much of a transition metal on the surface thereof some of the particles can be removed from the system 101 while make-up particles can be introduced into the system 101.

In some examples, an oxidant stream via line 1039 and a steam stream via line 1023 can be introduced or otherwise fed into the gasifier 1027. The oxidant, steam, and particles having the coke formed on the surface thereof can be contacted within a gasification zone 1029 within the gasifier 1027 to effect gasification of at least a portion of the coke disposed on the surface of the particles to produce a gasification zone effluent. The gasification zone effluent can include heated and regenerated particles and a synthesis gas. The synthesis gas can include hydrogen, carbon monoxide, and carbon dioxide. The heated and regenerated particles via line or channel 1031 can be discharged or otherwise obtained from the gasifier 1027 and can be recycled to the pyrolysis reactor 1007 to provide at least a portion of the heated particles introduced thereto. A second gaseous stream rich in the synthesis gas can be discharged or otherwise obtained via line 1033 from the gasifier 1027.

As shown, the oxidant stream in line 1039 can be discharged or otherwise obtained from an air separation unit 1037. More particularly, an air stream via line 1035 can be introduced or otherwise fed into the air separation unit 1037 and the oxidant stream via line 1039 and a nitrogen rich stream via line 1041 can be discharged or otherwise obtained from the air separation unit 1037. It should be understood that the air separation unit 1037 is optional and an oxidant stream that includes air can be introduced into the gasifier 1027. The air separation unit 1037 can be or can include, but is not limited to, a cryogenic air separation unit, a membrane separation unit, a pressure swing adsorption unit, a vacuum pressure swing adsorption unit, and/or any other device or system capable of separating oxygen and nitrogen from air.

In some examples, a hydrocarbon fuel stream via line 1025 can be introduced into the gasifier 1027. The hydrocarbon fuel stream in line 1025 can be or can include, but is not limited to, methane, ethane, propane, natural gas, a fuel gas such as a mixture of one or more $C_1$-$C_5$ hydrocarbons, resid, pyrolysis tar, or a mixture thereof. In some examples, at least a portion of the hydrocarbon fuel stream can be combusted, subject to reforming in the presence of the steam, or both within the gasification zone 1029 to produce additional heat and/or synthesis gas.

In some examples the second gaseous stream rich in the synthesis gas via line 1033 can be introduced into the heat exchange stage 1043 to produce a cooled or quenched second gaseous stream via line 1045. The cooled second gaseous stream in line 1045 can be rich in the synthesis gas and can include condensed or liquid water. The second gaseous stream rich in the synthesis gas in line 1033 can be indirectly cooled by transferring heat from the second gaseous stream to a cooling medium, by direct contact with a cooling medium, or a combination thereof. In some examples, particles entrained in the second gaseous stream in line 1045 can also be present in the condensed water. The cooled second gaseous stream via line 1045 can be introduced or otherwise fed into the separation stage 1047 to separate at least a portion of the condensed water and, if present, particles via line 1051. A dried or water-lean second gaseous stream via line 1049 can be discharged or otherwise obtained from the separation stage 1047.

In some examples, the synthesis gas in line 1033 can also include hydrogen sulfide. In such examples, the water-lean second gaseous stream via line 1049 can be introduced into a hydrogen sulfide removal stage 1053. A purified second gaseous stream via line 1055 and a hydrogen sulfide rich stream via line 1057 can be discharged or otherwise obtained from the hydrogen sulfide removal stage 1053. The purified second gaseous stream via line 1055 can be introduced or otherwise fed into the compression stage 1059 to produce a compressed second gaseous stream via line 1061.

At least a portion of the compressed second gaseous stream in line 1061 can be introduced or otherwise fed via line 1063 into a water gas shift stage 1069. Optionally, steam via line 1067 can be introduced or otherwise fed into the water gas shift stage 1069 to assist in producing additional molecular hydrogen. A shifted synthesis gas stream via line 1071 can be discharged or otherwise obtained from the water gas shift stage and introduced into the carbon dioxide separation stage 1073. Any convenient type of carbon dioxide separation can be used, such as cryogenic separation, membrane separation, and/or adsorption (including swing adsorption). In some examples, at least a portion of the compressed second gaseous stream in line 1061 can be introduced via line 1065 into the gasifier 1027 as a diluent. For example, if the air separation unit 1037 is used, the compressed second gaseous stream via line 1065 can be introduced to make up for at least a portion of the reduced content of molecular nitrogen that would have been present if air were introduced via line 1039 as the oxidant stream in to the gasifier 1027. In other examples, at least a portion of the carbon dioxide via line 1079 can be introduced into the gasifier 1027 as at least a portion of any diluent introduced thereto.

A carbon dioxide rich stream via line 1075 and a carbon dioxide lean synthesis gas stream via line 1077 can be discharged or otherwise obtained from the carbon dioxide separation stage. In some examples, at least a portion of the carbon dioxide rich stream in line 1075 can be introduced via line 1079 into storage for sequestration, utilized for enhanced oil recovery, or otherwise used rather than being emitted directly into the environment. In some examples, a portion of the carbon dioxide in line 1075 can be used to produce one or more chemicals. In one example, at least a portion of the carbon dioxide in line 1075 can be introduced via line 1081 into the urea synthesis unit 1083.

The carbon dioxide lean synthesis gas in line 1077 can be used to produce one or more chemicals and/or used as a source of molecular hydrogen. In some examples, at least a portion of the carbon dioxide lean synthesis gas in line 1077 can be introduced via line 1085 into an ammonia synthesis unit 1091. A nitrogen rich gas stream via line 1087 can also be introduced into the ammonia synthesis unit 1091. As shown, at least a portion of the nitrogen rich gas stream in line 1041 obtained from the optional air separation stage 1037 can be used, however any nitrogen gas stream can be used. Optionally, a hydrogen rich gas stream via line 1089 can also be introduced into the ammonia synthesis unit 1091. The carbon dioxide lean synthesis gas, the nitrogen rich gas stream, and the optional hydrogen rich gas stream can be exposed to an ammonia synthesis catalyst under ammonia synthesis conditions within the ammonia synthesis unit 1091 to produce ammonia via line 1093. If the system 101 includes the optional air separation stage 1037 and all of the nitrogen rich stream in line 1041 cannot be used then at least a portion of the nitrogen rich gas stream in line 1041 can be removed via line 1095 from the system 101.

In some examples, at least a portion of the carbon dioxide lean synthesis gas in line 1077 can be introduced via line 1097 into the methanol synthesis unit 1099. The carbon dioxide lean synthesis gas can be exposed to a methanol synthesis catalyst under methanol synthesis conditions to produce methanol within the methanol synthesis unit 1099. A methanol product via line 1101 can be discharged or otherwise obtained from the methanol synthesis unit 1099.

In some examples, as least a portion of the carbon dioxide lean synthesis gas in line 1077 can be removed from the system via line 1103 and used as a hydrogen rich gas stream in one or more processes or as a low carbon emitting fuel gas. For example, the carbon dioxide lease synthesis gas in line 1103 can be a relatively pure molecular hydrogen stream that can be used in hydroprocessing a hydrocarbon, used as the optional hydrogen that can be introduced via line 1089 into the ammonia synthesis unit 1091, and/or used in any other process that can use molecular hydrogen.

In some example, at least a portion of the ammonia product in line 1093 can be introduced via line 1105 into the urea synthesis unit 1083. The ammonia and the carbon dioxide can be exposed to reaction conditions sufficient to produce urea within the urea synthesis unit 1083. A urea product via line 1107 can be discharged otherwise obtained from the urea synthesis unit 1083. It should be understood that a carbon dioxide rich stream or an ammonia product can be brought in external from the system 101 and introduced into the urea synthesis unit 1083 to produce the urea product via line 1103. In some examples, at least a portion of the ammonia produce in line 1093 can be removed via line 1109.

Listing of Embodiments

This disclosure may further include the following non-limiting embodiments.

A1. A process for converting a hydrocarbon-containing feed by pyrolysis and gasification, comprising: (I) feeding the hydrocarbon-containing feed and heated particles into a pyrolysis zone; (II) contacting the hydrocarbon-containing feed with the heated particles in the pyrolysis zone to effect pyrolysis of at least a portion of the hydrocarbon-containing feed to produce a pyrolysis zone effluent comprising olefins and the particles, wherein coke is formed on the surface of the particles, and wherein a velocity of gaseous components within the pyrolysis zone is at least 20% greater than a velocity of the particles within the pyrolysis zone; (III) obtaining from the pyrolysis zone effluent a first gaseous stream rich in the olefins and a first particle stream rich in the particles; (IV) feeding at least a portion of the first particle stream, an oxidant stream, and a steam stream into a gasification zone; (V) contacting the first particle stream, the oxidant stream, and the steam stream within the gasification zone to effect gasification of at least a portion of the coke disposed on the surface of the particles to produce a gasification zone effluent comprising heated and regenerated particles and a synthesis gas, wherein the synthesis gas comprises molecular hydrogen, carbon monoxide, and carbon dioxide; (VI) obtaining from the gasification zone effluent a second gaseous stream rich in the synthesis gas and a second particle stream rich in the heated and regenerated particles; and (VII) feeding at least a portion of the second particle stream into the pyrolysis zone as at least a portion of the heated particles fed into the pyrolysis zone in step (I).

A2. The process of A1, further comprising: (VIII) converting at least a portion of the carbon monoxide in the second gaseous stream and steam to carbon dioxide to produce a shifted synthesis gas stream; and (IX) obtaining from the shifted synthesis gas stream a carbon dioxide lean synthesis gas stream and a carbon dioxide rich stream.

A3. The process of A2, further comprising, after step (VI) and before step (VIII), the following steps: (VIb) indirectly transferring heat from the second gaseous stream to a cooling medium to produce a cooled second gaseous stream comprising water; (VIc) separating at least a portion of the water and, if present, at least a portion of any regenerated particles and, if present, at least a portion of any hydrogen sulfide from the cooled second gaseous stream to produce a purified second gaseous stream; and (VId) compressing at least a portion of the purified second gaseous stream to produce a compressed second gaseous stream, wherein in step (VIII) the at least a portion of the carbon monoxide in the compressed second gaseous stream is converted to carbon dioxide to produce the shifted synthesis gas stream.

A4. The process of any of A1 to A3, further comprising (X) separating the oxidant stream and a nitrogen stream from an air stream, wherein the oxidant stream comprises 40 vol % or more of molecular oxygen, and wherein the nitrogen stream comprises 60 vol % or more of molecular nitrogen.

A5. The process of any of A2 to A4, further comprising (XI) exposing at least a portion of the carbon dioxide lean synthesis gas stream to an ammonia synthesis catalyst under ammonia synthesis conditions to produce ammonia.

A6. The process of A5, further comprising (XII) exposing at least a portion of the ammonia and at least a portion of the carbon dioxide rich stream to reaction conditions sufficient to produce urea.

A7. The process of any of A2 to A6, further comprising: (XIII) exposing at least a portion of the carbon dioxide lean synthesis gas stream to a methanol synthesis catalyst under methanol synthesis conditions to produce methanol.

A8. The process of any of A2 to A7, further comprising (XIV) obtaining from the carbon dioxide lean synthesis gas stream a hydrogen rich stream and a nitrogen rich stream, wherein the hydrogen rich stream comprises at least 20 vol % of molecular hydrogen.

A9. The process of A8, further comprising (XV) contacting at least a portion of the hydrogen rich stream and a hydrocarbon feed stream in the presence of a hydroprocessing catalyst to produce a hydrotreated product.

A10. The process of any of A2 to A9, further comprising (XVI) feeding at least a portion of the carbon dioxide rich stream into a subterranean formation to enhance a recovery of oil therefrom, feeding at least a portion of the carbon dioxide rich stream into a storage location for sequestration, usage, conversion, or a combination thereof.

A11. The process of any of A1 to A10, wherein the oxidant stream comprises molecular oxygen.

A12. The process of any of A1 to A11, wherein step (IV) further comprises feeding a hydrocarbon fuel stream into the gasification zone.

A13. The process of A12, wherein the hydrocarbon fuel stream comprises methane, ethane, propane, natural gas, a fuel gas such as a mixture of one or more $C_1$-$C_5$ hydrocarbons, resid, pyrolysis tar, or a mixture thereof.

A14. The process of A12 or A13, wherein a first portion of the hydrocarbon fuel stream is combusted within the gasification zone, and wherein a second portion of the hydrocarbon fuel steam is converted into molecular hydrogen and carbon monoxide.

A15. The process of any of A12 to A14, wherein the hydrocarbon fuel stream is introduced into the gasification zone at a location downstream of where the oxidant stream and the first particle stream are introduced into the gasification zone.

A16. The process of any of A12 to A15, wherein 99 wt % to 100 wt % of a carbon content of the hydrocarbon fuel stream is converted into carbon monoxide, carbon dioxide, or both within the gasification zone.

A17. The process of any of A1 to A16, wherein 80 wt % to 100 wt % of the coke on the surface of the particles is combusted within the gasification zone.

A18. The process of any of A1 to A17, wherein 99 wt % to 100 wt % of a carbon content of the coke on the surface of the particles is converted into carbon monoxide, carbon dioxide, or both within the gasification zone.

A19. The process of any of A1 to A18, wherein step (IV) further comprises feeding a diluent stream into the gasification zone.

A20. The process of A19, wherein the diluent stream comprises the second gaseous stream obtained in step (VI) or comprises the compressed second gaseous stream obtained in step (VId), or a mixture thereof.

A21. The process of A19 or A20, wherein the diluent stream comprises at least a portion of the carbon dioxide rich stream.

A22. The process of any of A1 to A21, wherein the synthesis gas further comprises molecular nitrogen, wherein, on a volume basis, the synthesis gas comprises a greater amount of molecular hydrogen than molecular nitrogen.

A23. The process of any of A1 to A22, wherein the second gaseous stream comprises 10 wt % to 20 wt % of molecular hydrogen, 15 wt % to 25 wt % of carbon monoxide, and 5 wt % to 15 wt % of carbon dioxide.

A24. The process of any of A1 to A22, wherein the second gaseous stream comprises 10 wt % to 25 wt % of molecular hydrogen, 15 wt % to 30 wt % of carbon monoxide, and at least 5 wt % of carbon dioxide, based on the total amount of the molecular hydrogen, the carbon monoxide, and the carbon dioxide.

A25. The process of any of A1 to A24, wherein the oxidant stream comprises air or a fraction of air, and wherein, on a volume basis, a total amount of molecular oxygen to a total amount of molecular nitrogen within the gasification zone is at least 0.26:1.

A26. The process of any of A1 to A25, wherein the pyrolysis zone is operated at a temperature of 800° C. to 1,100° C.

A27. The process of any of A1 to A26, wherein a velocity of the gaseous components is in a range of 9 m/s to 155 m/s within the pyrolysis zone, and wherein a velocity of the particles is up to 15.5 m/s within the pyrolysis zone.

A28. The process of any of A1 to A27, wherein the hydrocarbon-containing feed is contacted with the heated particles within the pyrolysis zone for a gas residence time of 10 milliseconds to 2,000 milliseconds.

A29. The process of any of A1 to A28, wherein the hydrocarbon-containing feed is contacted with the heated particles within the pyrolysis zone for a gas residence time of 10 milliseconds to 700 milliseconds.

A30. The process of any of A1 to A29, wherein the contacting in the pyrolysis zone in step (II) is performed under a pressure from 200 kPa-absolute to 1,000 kPa-absolute.

A31. The process of any of A1 to A30, wherein the particles have an average size of 50 μm to 500 μm.

A32. The process of any of A1 to A31, further comprising feeding a steam stream into the pyrolysis zone in step (I).

A33. The process of A32, wherein a weight ratio of the steam stream to the hydrocarbon-containing feed fed into the pyrolysis zone is 0.01:1 to 6:1 (preferably 0.1:1 to 1:1).

A34. The process of any of A1 to A33, wherein a weight ratio of the particles to the hydrocarbon-containing feed stream fed into the pyrolysis zone in step (I) is 10:1 to 50:1 (preferably 10:1 to 20:1).

A35. The process of any of A1 to A34, wherein the particles fed into the pyrolysis zone in step (I) comprise an oxide of a transition metal element capable of oxidizing molecular hydrogen within the pyrolysis zone.

A36. The process of A35, wherein at least a portion of the transition metal element in the particles in the first particle stream rich in the particles is at a reduced state compared to the transition metal element in the particles fed into the pyrolysis zone.

A37. The process of A35 or A36, wherein the transition metal element is selected from titanium, vanadium, chromium, manganese, iron, cobalt, niobium, nickel, molybdenum, tantalum, tungsten, alloys thereof, and a mixture thereof.

A38. The process of any of A35 to A37, wherein the transition metal element has a concentration of 500 ppmw to 50 wt % (preferably 2 wt % to 30 wt %), based on a total weight of the particles.

A39. The process of any of A35 to A38, wherein the oxide of the transition metal element favors the oxidation of hydrogen over the oxidation of hydrocarbons in the pyrolysis zone.

A40. The process of any of A35 to A39, wherein at least a portion of the particles are derived from a fluid catalytic converter catalyst.

A41. The process of any of A1 to A40, wherein the particles comprise silica, alumina, titania, zirconia, magnesia, pumice, ash, clay, diatomaceous earth, bauxite, or a mixture thereof.

A42. The process of any of A1 to A41, wherein the gasification zone is operated at a temperature of at least 1,000° C. and a pressure of 100 kPa-gauge to 1,000 kPa-gauge.

A43. The process of any of A1 to A42, wherein the gasification zone is operated at a temperature of 1,200° C. to 1,500° C. and a pressure of 100 kPa-gauge to 1,000 kPa-gauge.

A44. The process of any of A3 to A43, wherein the second gaseous stream is at a temperature of 1,000° C. to 1,500° C., and wherein the cooled second gaseous stream is at a temperature of 10° C. to 100° C.

A45. The process of any of A3 to A44, wherein the compressed second gaseous stream is at a pressure of 1,100 kPa-gauge to 8,000 kPa-gauge.

B1. A system for upgrading a hydrocarbon-containing feed by pyrolysis and gasification, the system comprising: (i) a pyrolysis reactor having a pyrolysis zone adapted for receiving the hydrocarbon-containing feed and heated particles, allowing the hydrocarbon-containing feed to contact the particles to effect pyrolysis of at least a portion of the hydrocarbon-containing feed and to form coke on the surface of the particles to produce a pyrolysis zone effluent comprising olefins and the particles while maintaining a velocity of gaseous components within the pyrolysis zone that is at least 20% greater than a velocity of the particles within the pyrolysis zone; (ii) a first separation vessel adapted for receiving the pyrolysis zone effluent, optionally receiving a stripping steam stream, separating the pyrolysis zone effluent to obtain a first gaseous stream rich in the olefins and a first particle stream rich in the particles, discharging the first gaseous stream, and discharging the first particle stream; (iii) a first channel adapted for feeding at least a portion of the first particle stream to a gasification zone; (iv) a gasifier comprising the gasification zone, the gasification zone adapted for receiving the first particle stream, an oxidant stream, and a steam stream, and gasifying at least a portion of the coke disposed on the surface of the particles to produce a gasification zone effluent comprising heated and regenerated particles and a synthesis gas, wherein the synthesis gas comprises molecular hydrogen, carbon monoxide, and carbon dioxide, discharging a second gaseous stream rich in the synthesis gas, and discharging a second particle stream rich in the heated and regenerated particles; and (v) a second channel adapted for feeding at least a portion of the heated and regenerated particles to the pyrolysis reactor such that the regenerated and heated particles make up at least a portion of the heated particles contacted with the hydrocarbon-containing feed in the pyrolysis zone.

B2. The system of B1, further comprising: (vi) a compression stage adapted for compressing at least a portion of the second gaseous stream rich in the synthesis gas to produce a compressed second gaseous stream; (vii) a converter comprising a conversion zone containing a catalyst adapted for converting at least a portion of the carbon monoxide in the compressed second hydrocarbon rich stream to carbon dioxide to produce a shifted synthesis gas stream; and (viii) a second separation vessel adapted for receiving the shifted synthesis gas, separating at least a portion of the carbon dioxide from the shifted synthesis gas to obtain a carbon dioxide lean synthesis gas stream and a carbon dioxide rich gas stream, discharging the carbon dioxide lean synthesis gas stream, and discharging the carbon dioxide rich gas stream.

B3. The system of B1 or B2, further comprising a methanol reactor containing a methanol synthesis catalyst adapted for converting at least a portion of the carbon dioxide lean synthesis gas stream to methanol.

B4. The system of any of B1 to B3, further comprising an ammonia reactor adapted for receiving at least a portion of the carbon dioxide lean synthesis gas stream, the ammonia reactor containing an ammonia synthesis catalyst adapted for converting at least a portion of the carbon dioxide lean synthesis gas stream to ammonia.

B5. The system of any of B1 to B4, further comprising a urea reactor adapted for receiving at least a portion of the ammonia and at least a portion of the carbon dioxide rich gas stream, the urea reactor adapted for converting at least a portion of the carbon dioxide rich gas stream and at least a portion of the ammonia into urea.

B6. The system of any of B1 to B5, further comprising a hydroprocessor adapted for receiving at least a portion of the carbon dioxide lean synthesis gas stream and a hydrocarbon feed, the hydroprocessor adapted to contact the carbon dioxide lean synthesis gas stream and the hydrocarbon feed in the presence of a hydroprocessing catalyst to produce a hydrotreated product. Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A process for converting a hydrocarbon-containing feed by pyrolysis and gasification, comprising:

(I) feeding the hydrocarbon-containing feed and heated particles into a pyrolysis zone;

(II) contacting the hydrocarbon-containing feed with the heated particles in the pyrolysis zone to effect pyrolysis of at least a portion of the hydrocarbon-containing feed to produce a pyrolysis zone effluent comprising olefins and the particles, wherein coke is formed on the surface of the particles, and wherein a velocity of gaseous components within the pyrolysis zone is at least 20% greater than a velocity of the particles within the pyrolysis zone;

(III) obtaining from the pyrolysis zone effluent a first gaseous stream rich in the olefins and a first particle stream rich in the particles;

(IV) feeding at least a portion of the first particle stream, an oxidant stream, and a steam stream into a gasification zone;

(V) contacting the first particle stream, the oxidant stream, and the steam stream within the gasification zone to effect gasification of at least a portion of the coke disposed on the surface of the particles to produce a gasification zone effluent comprising heated and regenerated particles and a synthesis gas, wherein the synthesis gas comprises molecular hydrogen, carbon monoxide, and carbon dioxide;

(VI) obtaining from the gasification zone effluent a second gaseous stream rich in the synthesis gas and a second particle stream rich in the heated and regenerated particles; (VII) feeding at least a portion of the second particle stream into the pyrolysis zone as at least a portion of the heated particles fed into the pyrolysis zone in step (I);

(VIII) converting at least a portion of the carbon monoxide in the second gaseous stream and steam to carbon dioxide to produce a shifted synthesis gas stream; and (IX) obtaining from the shifted synthesis gas stream a carbon dioxide lean synthesis gas stream and a carbon dioxide rich stream.

2. The process of claim 1, further comprising (X) separating the oxidant stream and a nitrogen stream from an air stream, wherein the oxidant stream comprises at least 40 vol % of molecular oxygen, and wherein the nitrogen stream comprises at least 60 vol % of molecular nitrogen.

3. The process of claim 1, further comprising (X) exposing at least a portion of the carbon dioxide lean synthesis gas stream to a methanol synthesis catalyst under methanol synthesis conditions to produce methanol.

4. The process of claim 1, further comprising (X) obtaining from the carbon dioxide lean synthesis gas stream a hydrogen rich stream and a nitrogen rich stream, wherein the hydrogen rich stream comprises at least 20 vol % of molecular hydrogen.

5. The process of claim 1, wherein a first portion of the coke on the surface of the particles is combusted within the gasification zone, and wherein a second portion of the coke on the surface of the particles and a portion of the steam are converted into molecular hydrogen and carbon monoxide within the gasification zone.

6. The process of claim 1, wherein step (IV) further comprises feeding a hydrocarbon fuel stream into the gasification zone, wherein a first portion of the hydrocarbon fuel stream is combusted within the gasification zone, and wherein a second portion of the hydrocarbon fuel stream is converted into molecular hydrogen and carbon monoxide.

7. The process of claim 1, wherein the synthesis gas further comprises molecular nitrogen, and wherein, on a volume basis, the synthesis gas comprises a greater amount of molecular hydrogen than molecular nitrogen.

8. The process of claim 1, wherein the second gaseous stream comprises 10 wt % to 25 wt % of molecular hydrogen, 15 wt % to 30 wt % of carbon monoxide, and at least 5 wt % of carbon dioxide, based on the total weight of the second gaseous stream.

9. The process of claim 1, wherein the oxidant stream comprises air or a fraction of air, and wherein, on a volume basis, a total amount of molecular oxygen to a total amount of molecular nitrogen within the gasification zone is at least 0.26:1.

10. The process of claim 1, further comprising feeding a steam stream into the pyrolysis zone in step (I), wherein:

a weight ratio of the steam stream to the hydrocarbon-containing feed fed into the within the pyrolysis zone is 0.01:1 to 6:1, the pyrolysis zone is operated at a temperature of 800° C. to 1,100° C., a pressure within the pyrolysis zone is from 200 kPa-absolute to 1,000 kPa-absolute, a velocity of the gaseous components within the pyrolysis zone is in a range of 9 m/s to 155 m/s, a velocity of the particles within the pyrolysis zone is up to 15.5 m/s, a weight ratio of the particles to the hydrocarbon-containing feed stream fed into the pyrolysis zone in step (I) is 10:1 to 50:1, and the hydrocarbon-containing feed is contacted with the heated particles within the pyrolysis zone for a gas residence time of 10 milliseconds to 700 milliseconds.

11. The process of claim 1, wherein the heated particles fed into the pyrolysis zone in step (I) comprise an oxide of a transition metal element capable of oxidizing molecular hydrogen within the pyrolysis zone, and wherein at least a portion of the transition metal element in the particles in the first particle stream rich in the particles is at a reduced state compared to the transition metal element in the particles fed into the pyrolysis zone.

12. The process of claim 1, wherein the gasification zone is operated at a temperature of 1,050° C. to 1,500° C. and a pressure of 100 kPa-gauge to 1,000 kPa-gauge.

13. The process of claim 1, wherein the hydrocarbon containing feed has a total carbon content, and wherein about 10 wt % to about 45 wt % of the total carbon content is converted into carbon dioxide and utilized in an enhanced oil recovery process, sequestered, converted into another compound, or a combination thereof.

14. The process of claim 1, wherein a velocity of the gaseous components within the pyrolysis zone is in a range of 9 m/s to 155 m/s.

15. The process of claim 1, wherein the hydrocarbon-containing feed contacts the plurality of fluidized particles within the pyrolysis reaction zone for a residence time of 1 ms to 2,000 ms.

16. The process of claim 1, wherein the heated particles are at a temperature of 800° C. to 1,500° C. when fed into the pyrolysis zone.

17. The process of claim 1, wherein the pyrolysis zone is located in a downflow reactor, and wherein the pyrolysis zone effluent is recovered from a bottom of the downflow reactor and introduced into a separation stage to obtain the first gaseous stream rich in the olefins and the first particle stream rich in the particles.

18. The process of claim 1, further comprising, after step (VI) and before step (VIII), the following steps:

(VIb) indirectly transferring heat from the second gaseous stream to a cooling medium to produce a cooled second gaseous stream comprising water;

(VIc) separating at least a portion of the water and, if present, at least a portion of any regenerated particles and, if present, at least a portion of any hydrogen sulfide from the cooled second gaseous stream to produce a purified second gaseous stream; and (VId) compressing at least a portion of the purified second gaseous stream to produce a compressed second gaseous stream, wherein in step (VIII) the at least a portion of the carbon monoxide in the compressed second gaseous stream is converted to carbon dioxide to produce the shifted synthesis gas stream.

19. The process of claim 18, wherein step (IV) further comprises feeding a diluent stream into the gasification zone, wherein the diluent stream comprises at least a portion of the second gaseous stream obtained in step (VI) or comprises at least a portion of the compressed second gaseous stream obtained in step (VId).

20. The process of claim 1, further comprising (X) exposing at least a portion of the carbon dioxide lean synthesis gas stream to an ammonia synthesis catalyst under ammonia synthesis conditions to produce ammonia.

21. The process of claim 20, further comprising (XI) exposing at least a portion of the ammonia and at least a portion of the carbon dioxide rich stream to reaction conditions sufficient to produce urea.

22. A process for converting a hydrocarbon-containing feed by pyrolysis and gasification, comprising:

(I) feeding the hydrocarbon-containing feed and heated particles into a pyrolysis zone;

(II) contacting the hydrocarbon-containing feed with the heated particles in the pyrolysis zone to effect pyrolysis of at least a portion of the hydrocarbon-containing feed to produce a pyrolysis zone effluent comprising olefins and the particles, wherein coke is formed on the surface of the particles, and wherein a velocity of gaseous components within the pyrolysis zone is at least 20% greater than a velocity of the particles within the pyrolysis zone;

(III) obtaining from the pyrolysis zone effluent a first gaseous stream rich in the olefins and a first particle stream rich in the particles;

(IV) feeding at least a portion of the first particle stream, an oxidant stream, and a steam stream into a gasification zone;

(V) contacting the first particle stream, the oxidant stream, and the steam stream within the gasification zone to effect gasification of at least a portion of the coke disposed on the surface of the particles to produce a gasification zone effluent comprising heated and regenerated particles and a synthesis gas, wherein the synthesis gas comprises molecular hydrogen, carbon monoxide, and carbon dioxide;

(VI) obtaining from the gasification zone effluent a second gaseous stream rich in the synthesis gas and a second particle stream rich in the heated and regenerated particles, wherein the second gaseous stream comprises 10 wt % to 25 wt % of molecular hydrogen, 15 wt % to 30 wt % of carbon monoxide, and at least 5 wt % of carbon dioxide, based on the total weight of the second gaseous stream; and (VII) feeding at least a portion of the second particle stream into the pyrolysis zone as at least a portion of the heated particles fed into the pyrolysis zone in step (I).

23. The process of claim 22, wherein the pyrolysis zone is located in a downflow reactor, and wherein the pyrolysis zone effluent is recovered from a bottom of the downflow reactor and introduced into a separation stage to obtain the first gaseous stream rich in the olefins and the first particle stream rich in the particles.

\* \* \* \* \*